United States Patent
Shih et al.

(10) Patent No.: US 9,599,612 B2
(45) Date of Patent: Mar. 21, 2017

(54) FLOW-BASED ENHANCEMENT OF SPECIFICITY FOR LABEL-FREE BIOCHEMICAL ASSAYS

(75) Inventors: Wan Y. Shih, Bryn Mawr, PA (US); Wei-Heng Shih, Bryn Mawr, PA (US); John-Paul McGovern, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 12/712,731

(22) Filed: Feb. 25, 2010

(65) Prior Publication Data

US 2010/0216172 A1  Aug. 26, 2010

Related U.S. Application Data

(60) Provisional application No. 61/155,560, filed on Feb. 26, 2009.

(51) Int. Cl.
| | | |
|---|---|---|
| *A61K 39/07* | (2006.01) | |
| *C07K 19/00* | (2006.01) | |
| *G01N 33/543* | (2006.01) | |
| *G01N 33/569* | (2006.01) | |

(52) U.S. Cl.
CPC . *G01N 33/54373* (2013.01); *G01N 33/56911* (2013.01); *G01N 2333/32* (2013.01)

(58) Field of Classification Search
None
See application file for complete search history.

(56) References Cited

U.S. PATENT DOCUMENTS

| | | | |
|---|---|---|---|
| 5,922,615 | A | 7/1999 | Nowakowski et al. |
| 7,458,265 | B2 | 12/2008 | Shih et al. |
| 2007/0089515 | A1* | 4/2007 | Shih et al. ............... 73/579 |
| 2008/0034840 | A1* | 2/2008 | Mutharasan et al. ...... 73/24.01 |
| 2010/0007330 | A1 | 1/2010 | Shih et al. |

FOREIGN PATENT DOCUMENTS

| | | | |
|---|---|---|---|
| WO | 2005005951 A2 | 1/2005 | |
| WO | WO 2007/007070 * | 1/2007 | ............ G01N 21/55 |
| WO | 2009046251 A2 | 4/2009 | |

OTHER PUBLICATIONS

McGovern et al. 2007 (In situ detection of *Bacillus anthracis* spores using fully submersible self-exciting, self-sensing PMN-PT/Sn piezoelectric microcantilevers; The Analyst, 132, 777-783).*
McGovern et al. 2008 (Label-free flow-enhanced specific detection of Bacillus anthracis using a piezoelectric microcantilever sensor; The Analyst, 133(5):649-654).*
Campbell et al. 2006 Detection of *Bacillus anthracis* spores and a model protein using PEMC sensors in a flow cell at 1 mL/min, Biosens. Bioelectron. 22 (2006) 78-85.*
Williams et al. 2003 (Species-Specific Peptide Ligands for the Detection of *Bacillus anthracis* Spores; Applied and Environmental Microbiology 69(10):6288-6293).*
McGovern et al. 2008 (Label-free low-enhanced specific detection of Bacillus anthracis using a piezoelectric microcantilever sensor; Analyst 133(5): 649-654).*
C. R. Tamanaha., et al., "Hybrid Macro-Micro Fluidics System for a Chip-Based Biosensor," Journal of Micromechanics and Microengineering, Institute of Physics Publishing, 2002, vol. 12, pp. 7-17.
W. L. Barnes, et al., "Surface Plasmon Subwavelength Optics," Nature, Aug. 14, 2003, vol. 424, pp. 824-830.

* cited by examiner

*Primary Examiner* — Gary Nickol
*Assistant Examiner* — Mary Lyons
(74) *Attorney, Agent, or Firm* — Mendelsohn Dunleavy, P.C.

(57) ABSTRACT

A label-free biochemical assay, in which label-free interrogation of a target-receptor layer is performed while the target-receptor layer is subjected to a relatively strong flow of an analyte-containing fluid. The volumetric flow rate for the assay is selected based on calibration data corresponding to the target substance, which advantageously results in fewer and/or smaller false-positive signals corresponding to non-target substances compared to those produced with the fluid being stationary. In various embodiments, the label-free interrogation method can be electro-mechanical and/or optical.

13 Claims, 8 Drawing Sheets

Table: Operating Parameters for Bio-Analytical System 100

| Target Size (μm) | Target Type | Flow Velocity Range (mm/s) | Minimum Cell Width (mm) | Maximum Cell Width (mm) |
|---|---|---|---|---|
| 0.001 | small molecules, peptides, oligonucleotides | 250-20,000 | 5E-05 | 8 |
| 0.01 | proteins, DNA, enzymes | 25-2,000 | 5E-04 | 80 |
| 0.1 | viruses | 2.5-200 | 0.005 | >100 |
| 1 | bacteria, spores | 0.25-20 | 0.05 | >100 |
| 5 | parasites | 0.05-4 | 0.25 | >100 |
| 20 | cells, parasites | 0.0125-1 | 1 | >100 |
| 50 | cells | 0.005-0.4 | 2.5 | >100 |

FLOW-BASED ENHANCEMENT OF SPECIFICITY FOR LABEL-FREE BIOCHEMICAL ASSAYS

CROSS-REFERENCE TO RELATED APPLICATIONS

This application claims priority from U.S. Provisional Patent Application No. 61/155,560 filed Feb. 26, 2009, and entitled "Label-Free Flow-Enhanced Specific Detection of *Bacillus Anthracis* Using a Piezoelectric Microcantilever Sensor," which application is incorporated herein by reference in its entirety.

STATEMENT OF GOVERNMENTAL INTEREST

This invention was made with government support under Contract No. R01 EB000720 awarded by the National Institutes of Health. The government has certain rights in the invention.

BACKGROUND

Field of the Invention

The present invention relates to bio-analytical systems and, more specifically but not exclusively, to flow-based enhancement of specificity for label-free biochemical assays.

Description of the Related Art

This section introduces aspects that may help facilitate a better understanding of the invention(s). Accordingly, the statements of this section are to be read in this light and are not to be understood as admissions about what is in the prior art or what is not in the prior art.

An assay is a procedure in molecular biology that is used to test for and/or measure the activity of a drug or a biochemical in an organism or a biological sample. Various types of biochemical assays, such as immunoassays, DNA-hybridization assays, and receptor-based assays, are widely used to detect trace quantities of specific target substances contained in the sample. For example, an immunoassay uses specific binding of an antibody to its antigen to measure the concentration of a target substance in a biological liquid. Either the antigen or the antibody can serve as the target substance. Other types of assays similarly use other types of specific binding.

A representative biochemical assay employs a solid substrate whose surface is coated with receptors having a relatively high specific binding affinity to a desired target substance. When a liquid sample containing the target substance is applied to the surface, the high specific binding affinity causes the receptors to capture the target substance. A common approach to detecting the captured target substance is to chemically attach to it a label that can be used to generate an observable signal. For example, a label can include a radioactive isotope, an enzyme, a fluorescent molecule, and/or a magnetic particle. The label can be attached to the captured target substance using any suitable means, such as covalent or electrostatic bonding and high-affinity molecular recognition of an exposed part of the target substance. The attached label is then detected using an appropriate detection means corresponding to the type of the label, thereby providing a measure of the concentration of the target substance in the sample.

One problem with biochemical assays in general is the presence of false-positive signals. For example, in the above-described label-based biochemical assays, false positives might originate from non-specific binding of labels to the surface of the solid substrate. Further complications arise when the sample contains several similar or related substances, with the target substance being only one of them. Due to the similarity to the target substance, the related non-target substances might bind, non- or semi-specifically, to the target receptors and then similarly bind the labels, thereby causing a corresponding false-positive signal.

SUMMARY

Disclosed herein are various embodiments of a label-free biochemical assay, in which label-free interrogation of a target-receptor layer is performed while the target-receptor layer is subjected to a relatively strong flow of an analyte-containing fluid. The volumetric flow rate for the assay is selected based on calibration data corresponding to the target substance, which advantageously results in fewer and/or smaller false-positive signals corresponding to non-target substances compared to those produced with the fluid being stationary. In a representative embodiment, the label-free interrogation method can be electro-mechanical and/or optical.

According to one embodiment, provided is a method of analyzing an analyte having the step of exposing a target-receptor layer to a fluid. The target-receptor layer comprises a plurality of target receptors adapted to bind a target substance. The fluid comprises the analyte. The method further has the step of performing label-free interrogation of the target-receptor layer for a presence of the target substance bound thereto while subjecting the target-receptor layer to a flow of the fluid.

According to another embodiment, provided is a bio-analytical system comprising means for exposing a target-receptor layer to an analyte-containing fluid. The target-receptor layer comprises a plurality of target receptors adapted to bind a target substance. The fluid comprises the analyte. The system further comprises means for performing label-free interrogation of the target-receptor layer for a presence of the target substance bound thereto while subjecting the target-receptor layer to a flow of the analyte-containing fluid.

BRIEF DESCRIPTION OF THE DRAWINGS

Other aspects, features, and benefits of various embodiments of the invention will become more fully apparent, by way of example, from the following detailed description and the accompanying drawings, in which.

DETAILED DESCRIPTION

Enhancement of Specificity in a Cantilever-Based Bio-Analytical System

Figure 1A:
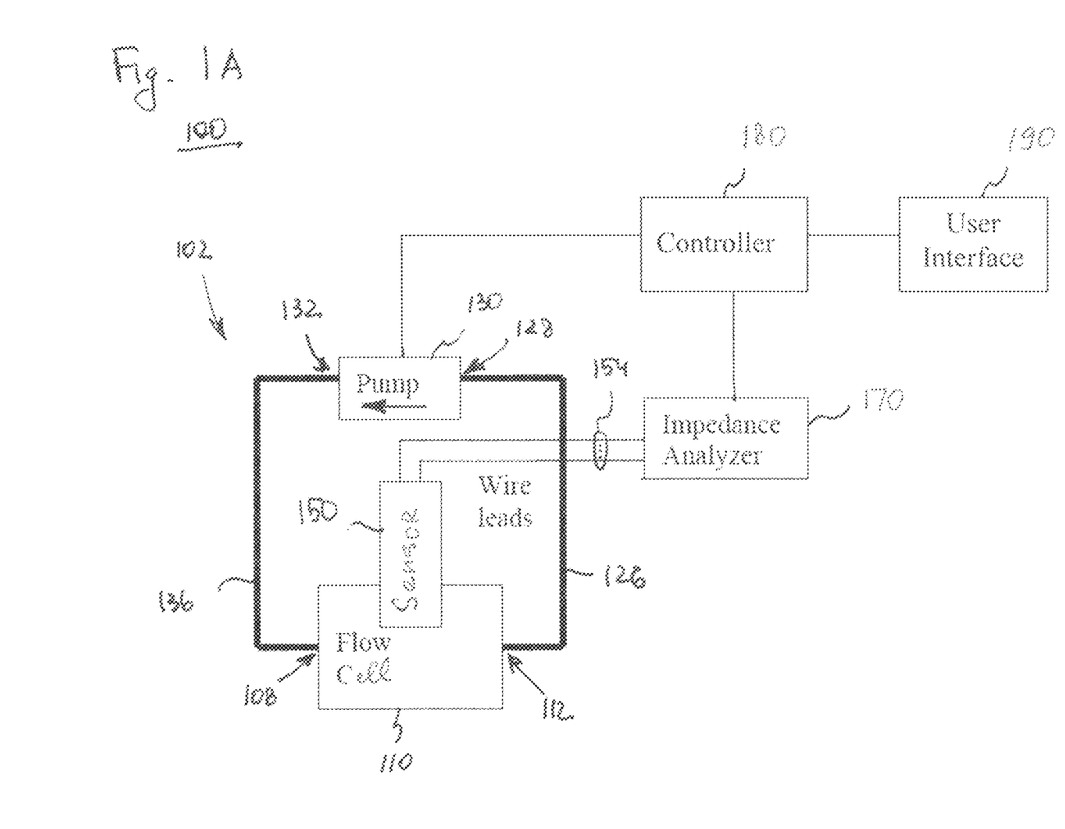
FIGS. 1A-C show a bio-analytical system according to one embodiment of the invention.
Figure 1B:
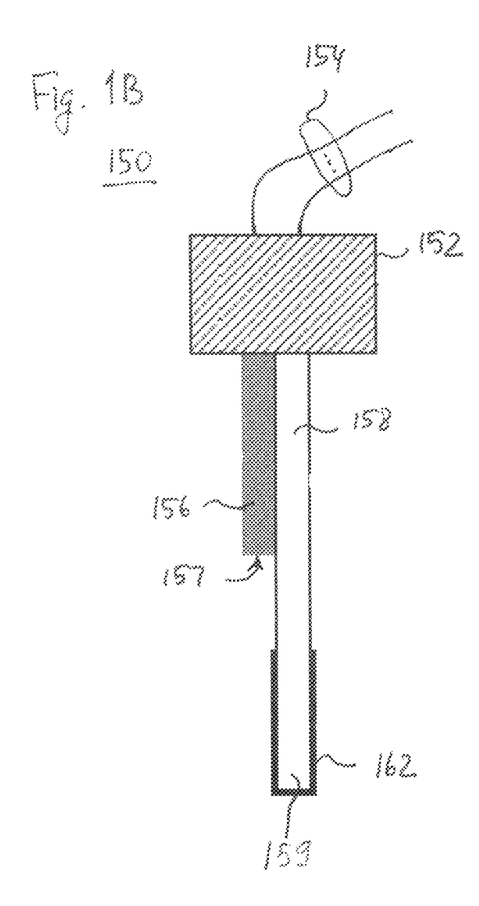
Figure 1C:
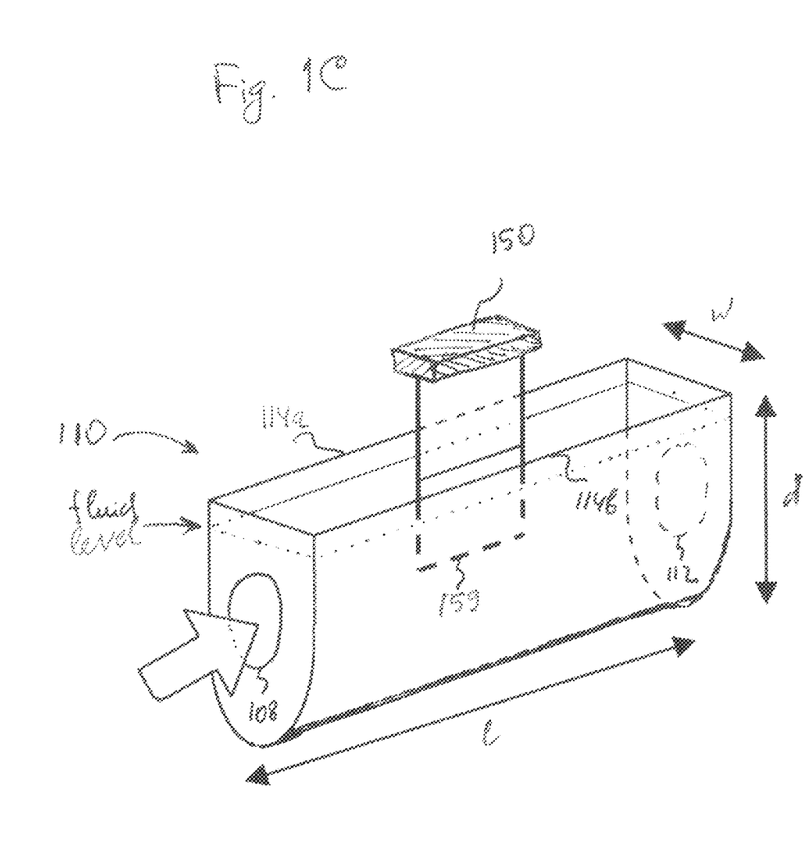

FIGS. 1A-C show a bio-analytical system 100 according to one embodiment of the invention. More specifically, FIG. 1A shows a block diagram of bio-analytical system 100. FIG. 1B shows a side view of a cantilever sensor 150 used in bio-analytical system 100. FIG. 1C shows a perspective three-dimensional view of a flow cell 110 used in bio-analytical system 100, with cantilever sensor 150 positioned in the flow cell.

Referring to FIG. 1A, bio-analytical system 100 has an analyte-delivery subsystem 102 that has a pump 130 coupled to flow cell 110 and configured to pump an analyte-containing fluid through the flow cell. In the embodiment shown in FIG. 1A, analyte-delivery subsystem 102 is depicted as having a closed-loop configuration. More specifically, an output port 132 of pump 130 is connected, via a tube 136, to an input port 108 of flow cell 110, and an input port 128 of the pump is connected, via a tube 126, to an output port 112 of the flow cell. This connection between pump 130 and flow cell 110 creates a circulation loop that enables the pump to continuously circulate the same analyte-containing fluid through the flow cell. Analyte-delivery subsystem 102 might include several valves and/or fluid containers (not explicitly shown in FIG. 1A) for filling the circulation loop with a carrier fluid and/or injecting an analyte into the circulation loop, as known in the art. The closed-loop configuration of analyte-delivery subsystem 102 shown in FIG. 1A might be advantageous for detecting very low concentrations of target substances because sensor 150 is continuously re-exposed to the target substance, thereby facilitating its more-efficient binding to the corresponding target receptors of the sensor.

Alternatively, analyte-delivery subsystem 102 might have an open-loop configuration. An open-loop configuration can be produced from the closed-loop configuration of FIG. 1A, e.g., by replacing tube 126 with two tubes. One of these tubes is used to connect input port 128 of pump 130 to a supply container (not explicitly shown in FIG. 1A), while the other tube is used to connect output port 112 of flow cell 110 to a waste container (also not explicitly shown in FIG. 1A). The open-loop configuration of analyte-delivery subsystem 102 might be advantageous when a relatively large analyte-solution volume is available for analysis because the continuous flow of fresh analyte solution helps to attain and maintain a relatively high fill factor for the target-receptor layer of sensor 150.

Bio-analytical system 100 further has a user interface 190 that enables the user to make inputs and retrieve, analyze, and interpret the measurement results. User interface 190 is operatively coupled to a controller 180 that controls the operation of (i) pump 130 and (ii) an impedance analyzer 170. For example, based on user inputs and/or a configuration file, user interface 190 can send commands to controller 180, thereby causing the controller to (i) set a selected volumetric flow rate for pump 130, (ii) configure impedance analyzer 170 to execute a selected measurement routine, as might be appropriate for the particular type of sensor 150 deployed in flow cell 110, and (iii) send back to the user interface a report on the current status of the measurement.

In one embodiment, impedance analyzer 170 can be replaced by any suitable electrical unit that has an oscillator and a detector capable of measuring the phase shift between the input and output voltages (signals). User interface 190 can be a laptop or desktop computer.

Referring to FIGS. 1A and 1B, cantilever sensor 150 is coupled to impedance analyzer 170 via wire leads 154 that enable both electromechanical excitation of the sensor and electrical readout of the sensor's response to the excitation. Cantilever sensor 150 comprises a planar piezoelectric layer 156 attached to a planar non-piezoelectric structure 158. A clamp 152 encapsulates the rear ends of layer 156 and structure 158, as indicated in FIG. 1B. One function of clamp 152 is to provide structural support for layer 156 and structure 158, which by themselves might be relatively thin and delicate. Another function of clamp 152 is to protect and insulate the electrical connections between the electrodes attached to piezoelectric layer 156 and wire leads 154. In the embodiment shown in FIG. 1B, non-piezoelectric structure 158 protrudes past a distal edge 157 of piezoelectric layer 156. In an alternative embodiment, layer 156 and structure 158 might have an equal length so that edge 157 of layer 156 is aligned with the corresponding edge of structure 158.

Distal end 159 of structure 158 is a thin flexible plate that is coated with a target-receptor layer 162 on one or more sides as shown in FIG. 1B. Target-receptor layer 162 has a plurality of target receptors that are designed to have a relatively high specific-binding affinity to a target substance of interest. As used herein, the term "target receptor" refers to a chemical host that can recognize, e.g., stereo-specifically, a corresponding target substance and bind it as a guest via specific bonding and/or interactions between their complementary portions. The specific bonding and interactions might include, but are not limited to hydrogen bonding, metal coordination, hydrophobic forces, van der Waals forces, pi-pi interactions, and other electrostatic and/or electromagnetic interactions. Exemplary target-receptor/target-substance pairs are protein/ligand, antigen/antibody, DNA/protein, sugar/lectin, RNA/ribosome, RNA/aptamer, and protein/aptamer. Synthetic supramolecular systems that exhibit molecular recognition can also serve as target receptors.

In various alternative embodiments of cantilever sensor 150, one or more of the following modifications can be made to the structure shown in FIG. 1B. Non-piezoelectric structure 158 may be completely absent or be shorter than piezoelectric layer 156. The distal end of cantilever sensor 150 may be encapsulated by an electrical insulating layer and target-receptor layer 162 may be deposited over the electrical insulating layer. There may be an intermediate layer, such as a chromium-gold layer, between target-receptor layer 162 and the insulating layer. Target-receptor layer 162 may be deposited on both piezoelectric layer 156 and non-piezoelectric structure 158.

It is to be noted that the term "target receptor" should be construed in a broader sense than the term "receptor," as the latter term is used in conventional biochemistry. More specifically, in biochemistry, the term "receptor" usually refers to a protein molecule that is embedded, e.g., in a membrane or a cytoplasm of a cell. A molecule that binds to such a receptor is referred to as a ligand, and may be a peptide, a neurotransmitter, a hormone, a pharmaceutical drug, a toxin, or a pathogen. While protein "receptors" can certainly be adapted for use as "target receptors" in target-receptor layer 162, a target receptor of that layer is not necessarily a protein. Rather, as already indicated above, any suitable chemical host can be used as a target receptor in target-receptor layer 162.

Various surface-functionalization methods can be used to form target-receptor layer 162. For example, in one embodiment, distal end 159 of structure 158 can be functionalized using immobilization of glycidoxypropyltrimethoxysilane (GOPTS). GOPTS is a bi-functional linker that contains a trimethoxysilane group and a glycidoxy epoxide moiety. The trimethoxysilane group readily binds to glass or metallic-oxide surfaces, while leaving the glycidoxy epoxide moiety available for covalent binding to primary amines of an appropriately selected antibody. In another embodiment, distal end 159 of structure 158 can be functionalized by (i) depositing a layer of a noble metal, e.g., gold, over structure 158 or an encapsulating insulating layer (if present), (ii) treating the deposited metal layer with MPA (mercaptopropionic acid) to carboxylate its surface, and (iii) covalently binding an appropriately selected antibody to the carboxylic acid group to immobilize the antibody on the carboxylated surface. One skilled in the art will appreciate that other known surface-functionalization methods can similarly be used to form target-receptor layer 162.

Layer 156, structure 158, the encapsulating insulating layer (if present), and layer 162 are parts of a cantilever resonator that can be induced to vibrate by configuring impedance analyzer 170 to apply an appropriate ac drive signal to piezoelectric layer 156. The geometry and other relevant properties of layer 156, structure 158, the encapsulating insulating layer (if present), and layer 162 determine the resonance frequencies of the cantilever resonator, which can be measured, e.g., by sweeping the frequency of the ac drive signal over an appropriate frequency range and measuring the relative phase of the induced mechanical oscillation. Since the bound target substance changes the properties of target-receptor layer 162, the binding event manifests itself as a shift of a resonance frequency, which is detected by impedance analyzer 170 and quantified and interpreted using user interface 190. Due to the intrinsically high sensitivity of the resonance frequency to binding-induced changes in target-receptor layer 162, cantilever sensor 150 does not require the use of labels and is generally operated to implement label-free assays. In effect, bio-analytical system 100 performs label-free electromechanical interrogation of target-receptor layer 162 for a presence of the corresponding target substance bound thereto.

Suitable cantilever resonators that can be used in various embodiments of cantilever sensor 150 are disclosed, e.g., in U.S. Pat. No. 7,458,265, which is incorporated herein by reference in its entirety. A phase-shift detector that can be used as impedance analyzer 170 is disclosed, e.g., in U.S. Patent Application Publication No. 2010/0007330, which is also incorporated herein by reference in its entirety.

Referring to FIG. 1C, cantilever sensor 150 is positioned with respect to flow cell 110 so that target-receptor layer 162 is at least partially submerged in the fluid that flows through the cell from input port 108 to output port 112. Flow cell 110 might or might not have a cover (top wall). If flow cell 110 does not have a cover, then precautions are taken to maintain an appropriate fluid level in the cell, as indicated in FIG. 1C.

In a representative embodiment, the dimensions of flow cell 110, i.e., length l, depth d, and width w, are selected so that a laminar-flow regime can be implemented. As known in the art, laminar flows occur for Reynolds numbers smaller than about 2000. In one embodiment, depth d of flow cell 110 is at least as large as width w, and pump 130 is configured to provide a flow rate that results in a Reynolds number between about 0.1 and about 100.

A laminar flow typically has a parabolic velocity profile across the flow channel. This means that the flow velocity in flow cell 110 is close to zero near each of sidewalls 114a-b and near the bottom of the cell. The flow-velocity profile has a maximum in the middle portion of flow cell 110 and is characterized by a very small velocity gradient in the transverse direction near the center of the cell. In a representative configuration, cantilever sensor 150 is inserted into flow cell 110 so that (i) the larger facets of structure 158 are parallel to and equidistant from sidewalls 114a-b and (ii) the distance between distal end 159 and the bottom of the flow cell is at least d/2. In general, it might be advantageous to position cantilever sensor 150 so that target-receptor layer 162 is separated from the nearest sidewall 114 by a distance that is at least w/4. It might also be advantageous to position cantilever sensor 150 so that target-receptor layer 162 is separated from the cover and/or bottom of flow cell 110 by a distance that is at least d/4.

Figure 2A:
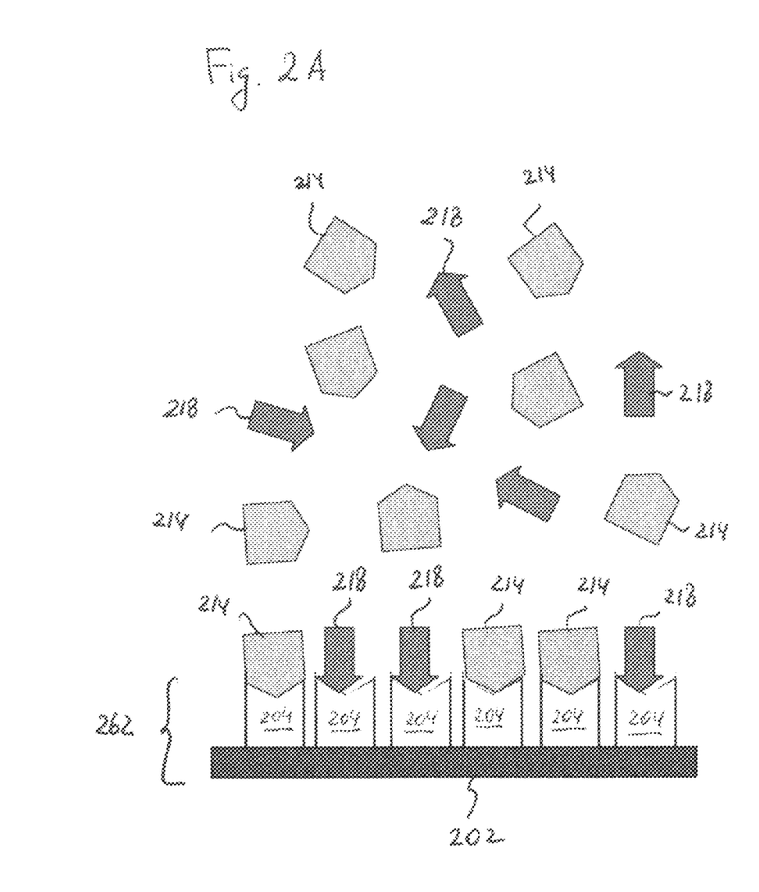
FIGS. 2A-B schematically represent flow-based enhancement of specificity achieved in the bio-analytical system of FIG. 1 according to one embodiment of the invention.
Figure 2B:
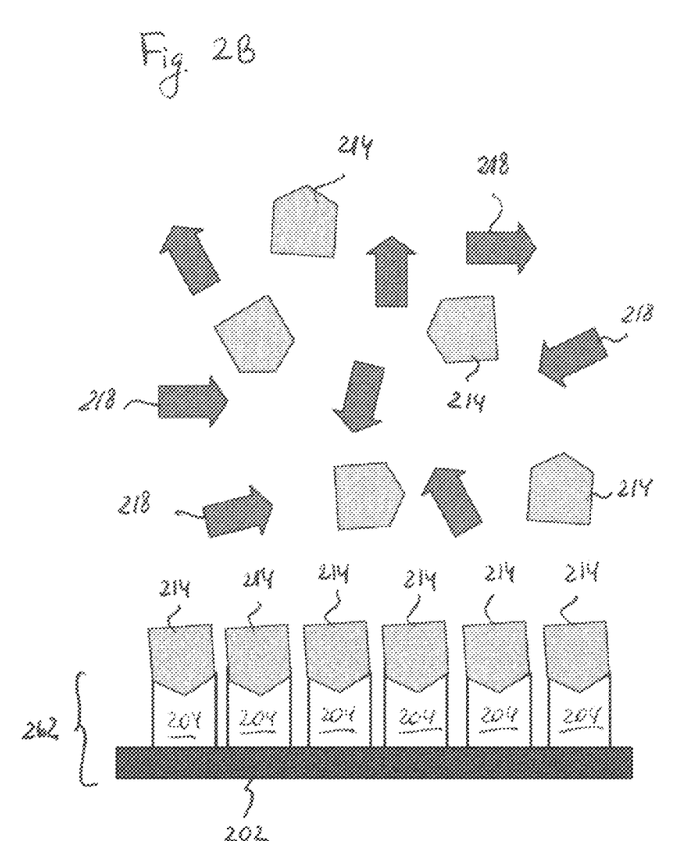

FIGS. 2A-B pictorially show flow-based enhancement of specificity achieved in bio-analytical system 100 according to one embodiment of the invention. More specifically, FIG. 2A is a cartoon that depicts a target-receptor layer 262 exposed to a stationary (e.g., not flowing) analyte-containing fluid. FIG. 2B is a similar cartoon that depicts target-receptor layer 262 exposed to an analyte-containing fluid that flows with respect to the target-receptor layer in an optimal manner.

Target-receptor layer 262 represents an exemplary embodiment of target-receptor layer 162 (see FIG. 1B) and comprises a plurality of target receptors 204 attached to a metal film 202. Target receptors 204 are designed to recognize and specifically bind a target substance 214, which can be, e.g., a protein molecule, a pathogen, or a toxin. The analyte-containing fluid to which target-receptor layer 262 is exposed has two substances dissolved or suspended in it. One of these substances is target substance 214. The other substance is a non-target substance 218 that can interfere with the detection of target substance 214 by semi-specifically binding to target receptors 204, as indicated in FIG. 2A.

Bio-analytical system 100 exploits the difference between the binding strengths of the specifically bound target substance 214 and the semi-specifically bound non-target substance 218 to enhance the specificity of detection of the target substance. More specifically, by appropriately selecting a volumetric flow rate for flow cell 110, bio-analytical system 100 subjects target-receptor layer 262 to a hydrodynamic drag force that is large enough to cause a release of most if not all of non-target substance 218 from target receptors 204 and yet small enough so that it does not cause a release of much if not any of target substance 214 from the target receptors. Target receptors 204 that become vacant due to the release of non-target substance 218 become available for binding target substance 214, as indicated in FIG. 2B. As a result, the "true" positive signal originating from the specifically bound target substance 214 is increased and the false-positive signal originating from the semi-specifically bound non-target substance 218 is significantly reduced, thereby improving the specificity of detection for the target substance.

It should be noted that bio-analytical system 100 operates to exert a hydrodynamic drag force directly onto the receptor-bound substance (e.g., semi-specifically bound non-target substance 218, FIG. 2A) without any assistance from a label (which is not used in the system and is typically absent). Another distinction from the prior art is that the hydrodynamic drag force is used in bio-analytical system 100 to remove, from the target-receptor layer, a non-target substance that has bound, non-specifically or semi-specifically, to the target receptors. In contrast, International Patent Application Publication No. WO 2005/005951 discloses flow-assisted removal of labels bound to the surface of the substrate (not removal of the non-target substance bound to the target receptors). Conceptual differences between a label and a non-target substance can be articulated, for example, as follows. A label is generally an artificially or synthetically produced entity that is deliberately added to the sample in the corresponding bio-analytical system with the purpose of binding to a particular receptor-bound target substance and making said target substance detectable by the specific detection means employed in the system. A non-target substance is usually originally present in the analyte and is sufficiently similar or related to the target substance so as to be able to bind to the target receptors, thereby blocking the target substance from binding to the target receptors.

To achieve best results in the detection of each particular target substance, bio-analytical system 100 is calibrated to determine optimal operating parameters. During a calibration procedure corresponding to a particular target substance, cantilever sensor 150 is exposed to one or more known concentrations of that target substance, and a response of the sensor is measured for a variety of flow rates. Then, similar measurements are performed for each of the non-target substances that are deemed likely to be present in actual analytes. The collected data are compared and analyzed, e.g., to identify an optimal flow rate or a range of flow rates at which cantilever sensor 150 yields acceptable ratios between the "true" positive signal corresponding to the target substance and the false-positive signals corresponding to the likely non-target substances. During normal operation, the calibration data are invoked to operate cantilever sensor 150 in an optimal flow regime, thereby achieving enhanced specificity and high statistical sensitivity in the detection of the target substance.

Figure 3A:
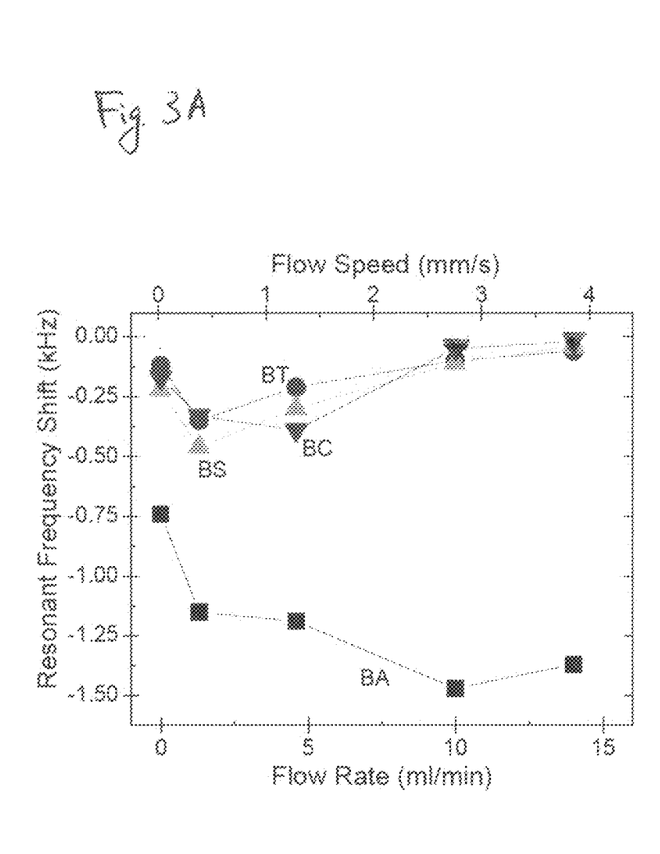
FIGS. 3A-B graphically show representative calibration data for the bio-analytical system of FIG. 1.
Figure 3B:
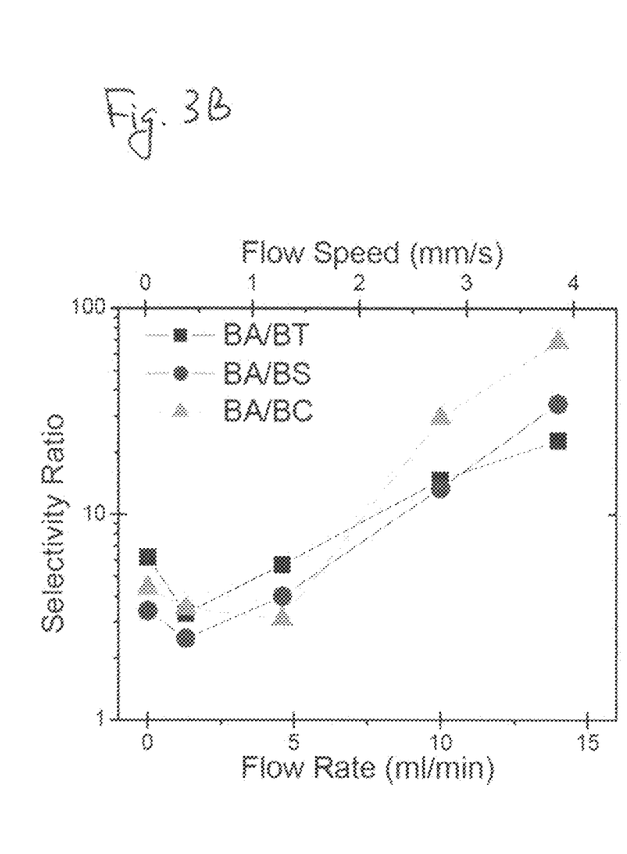

FIGS. 3A-B graphically show representative calibration data for bio-analytical system 100. More specifically, FIG. 3A graphically shows the dependence on the flow rate of the resonance frequency for cantilever sensor 150 functionalized for the detection of spores of Bacillus anthracis (BA, target substance) and then exposed to BA and its close relatives, B. thuringiensis, B. cereus, and B. subtilis (BT, BC, and BS, respectively; non-target substances). FIG. 3B graphically shows the dependence on the flow rate of the selectivity ratio for different substance pairs, each consisting of the target substance and one of the non-target substances.

The data of FIGS. 3A-B correspond to an embodiment of cantilever sensor 150 that was constructed by bonding, using electrically insulating epoxy, a 2 mm wide and 150 μm thick gold-coated glass wafer to a 2 mm wide and 127 μm thick PZT (piezoelectric-transducer) wafer. Prior to the bonding, a 10 nm thick chromium bonding layer was deposited, by e-beam evaporation, over the gold-coated glass wafer. The PZT wafer and the gold-coated glass wafer were attached to one another so that distal end 159 of the gold-coated glass wafer extended by about 1.7 mm past edge 157 of the PZT wafer (also see FIG. 1B). After wire leads 154 and clamp 152 were attached to the rear end of the bonded wafers, the resulting cantilever had a 0.5 mm long bonded PZT/glass portion and a 1.7 mm long gold-coated glass tip.

For anti-BA functionalization of the tip, the gold-coated glass tip was first cleaned with a diluted (1:40 in water) piranha solution, at 20° C. for 2 min. The cleaned tip was then incubated in 2 mM 3-mercaptopropionic acid (MPA), for 2 hours, to form an MPA monolayer on the gold surface. The carboxyl group of the MPA was then activated in a solution of 2 mM N-ethyl-N'-(3-dimethylaminopropyl)carbodiimide and 5 mM N-hydroxysuccinimide in water to allow covalent bonding of the primary amines on the anti-BA antibody to the MPA on the gold surface of the cantilever tip, which resulted in the formation of a target-receptor layer that was structurally similar to target-receptor layer 262 (FIG. 2).

Flow cell 110 had no cover. The flow cell also had a semi-circular bottom portion (with a radius of 4 mm) and the following overall dimensions: l=75 mm, w=8 mm, d=9 mm (also see FIG. 1C). The tip of the anti-BA functionalized cantilever was positioned in the center of flow cell 110 and submerged into the fluid by about 1 mm. The nominal volumetric flow rates were set at 0, 1.3, 4.6, 10, and 14 ml/min.

To characterize the responses of the anti-BA functionalized cantilever sensor 150, the tip of the cantilever was exposed, for a period of 30 minutes, to a suspension of spores, and the frequency shift versus time was recorded. The measurement was performed at each of the above-indicated volumetric flow rates for each of the substances of interest (i.e., BA, BT, BC, and BS). The spore concentration was about 20,000 spores/ml. It is known that, for many conventional assays, such as ELISA (Enzyme-Linked Immunosorbent Assay), this spore concentration is too low for reliable detection of the spores. In contrast, the anti-BA functionalized cantilever sensor 150 advantageously exhibits resonance-frequency shifts that can be detected accurately and reliably (see, e.g., FIG. 3A).

To quantify flow-based enhancement of specificity, the data shown in FIG. 3A were used to calculate a selectivity ratio, which was defined as a ratio of the resonance-frequency shift for the BA suspension and the resonance-frequency shift for a BX suspension (where X=T, C, or S), with both shifts detected at the end of a 30-min exposure to the corresponding spore suspension. The calculated selectivity ratios are graphically shown in FIG. 3B. The data of FIG. 3B show that, at relatively low flow rates, e.g., around 1.3 ml/min, the selectivity ratios are not as good as those obtained with the stationary analyte. However, the selectivity ratios markedly increase for flow rates between about 10 ml/min and about 15 ml/min to significantly exceed the corresponding stationary selectivity ratios. For example, the selectivity ratios for BA/BT, BA/BS, and BA/BC substance pairs advantageously increased from about 4.2, 3.5, and 6, respectively, at a zero flow rate to about 68, 35, and 24, respectively, at about 15 ml/min.

Based on the data shown in FIGS. 3A-B, a range of flow rates between about 10 ml/min and about 15 ml/min is designated as an optimal flow-rate range for this particular configuration of bio-analytical system 100. For subsequent operation of bio-analytical system 100 in this configuration, the user is therefore prompted to select a flow rate from this optimal range. As a result, cantilever sensor 150 can advantageously be operated in an optimal regime to provide enhanced specificity and high statistical sensitivity in the detection of BA.

Figure 4:
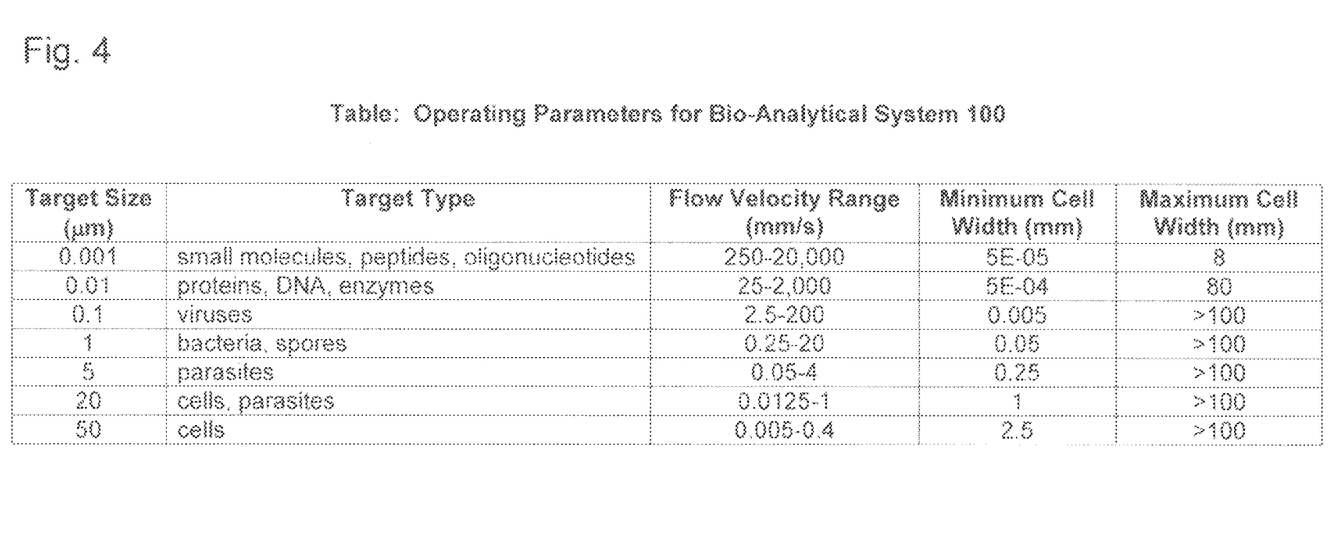
FIG. 4 shows a table listing approximate operating parameters that can be used to configure the bio-analytical system of FIG. 1 for the detection of different types of target substances.

FIG. 4 shows a table listing approximate operating parameters that can be used to configure bio-analytical system 100 for the detection of different types of target substances. More specifically, the table of FIG. 4 provides guidance for configuring bio-analytical system 100 to provide flow-based enhancement of specificity in the event of a likely presence of typical respective non-target substances in the analyte. The first two columns of the table list the sizes and general types, respectively, of various target substances to be detected using bio-analytical system 100. The third column lists the flow-velocity ranges within which flow-based enhancement of specificity can be achieved. The lower bound of the range corresponds to a linear velocity at which the hydrodynamic drag force of the flow begins to dislodge a typical (for the type) non-target substance from the target receptors of cantilever sensor 150. The upper bound of the range corresponds to a linear velocity at which the hydrodynamic drag force of the flow becomes large enough so that it begins to dislodge the target substance from the target receptors of cantilever sensor 150. The fourth and fifth columns of the table list representative dimensions of flow cell 110 that enable a typical compact, commercially available pump 130 to achieve the flow rates indicated in the third column.

Enhancement of Specificity in Other Bio-Analytical Systems

Although various embodiments of the invention have been described above in reference to cantilever-based bio-analytical system 100, flow-based enhancement of specificity can similarly be achieved in other bio-analytical systems. Two representative bio-analytical systems that implement label-free biochemical assays and lend themselves to flow-based enhancement of specificity are described in this subsection. One skilled in the art will appreciate that other label-free biochemical assays can also be implemented to achieve flow-based enhancement of specificity using various embodiments of the invention(s) described in this specification.

Figure 5:
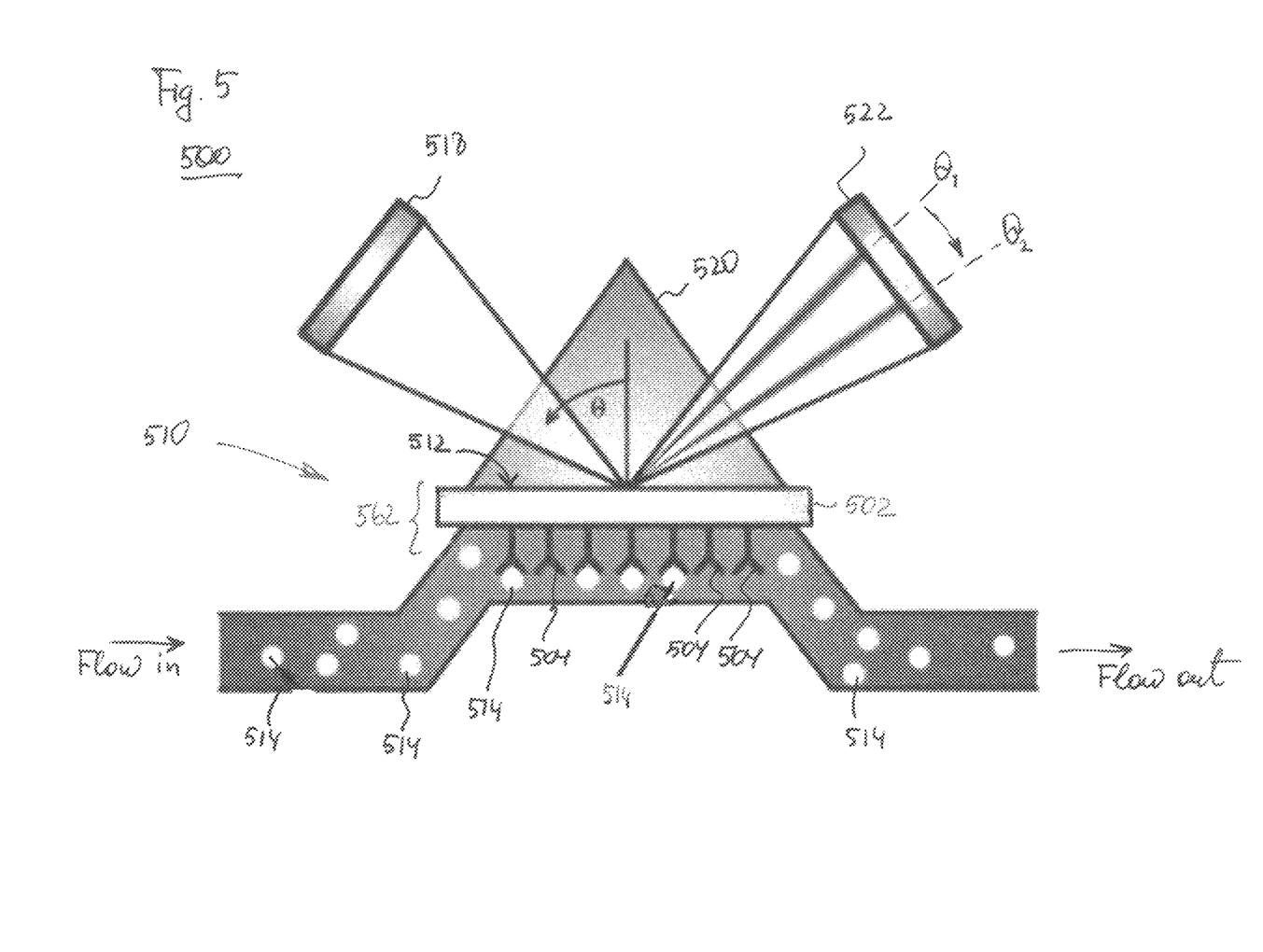
FIG. 5 schematically shows a bio-analytical system according to another embodiment of the invention.

FIG. 5 schematically shows a bio-analytical system 500 according to another embodiment of the invention. Similar to bio-analytical system 100 (FIG. 1), bio-analytical system 500 is adapted to provide flow-based enhancement of specificity in the detection of target substances. However, instead of cantilever-based detection, bio-analytical system 500 relies on surface plasmon resonance (SPR).

The term SPR refers to a phenomenon that can occur at a surface of a thin metal film, e.g., a gold film having a thickness of about 40 nm. At a small range of angles near the critical angle of reflection for the metal film, a portion of the incident light is transformed into surface plasmons (SPs). SPs, also often referred to as surface-plasmon polaritons, are surface-bound waves that can propagate, e.g., along a metal-dielectric interface or along a metal-vacuum interface. SPs can be qualitatively viewed as a combination of electromagnetic waves and associated charge waves. The electromagnetic waves propagate along the interface due to their interaction with free surface charges of the metal. The interaction also causes the surface charges to oscillate in resonance with the electromagnetic wave. The combined physical entity created via this resonant interaction, i.e., an entity including a charge wave and an electromagnetic wave, is an SP. The value of the incident angle at which SPs are generated in the most-efficient manner is very sensitive to the refractive index of the dielectric at the metal-dielectric interface due to the effects of surface-induced enhancement of the SP's evanescent electric field. A detailed description of pertinent physical properties of SPs can be found, e.g., in an article by W. L. Barnes, et al., entitled "Surface Plasmon Subwavelength Optics," published in Nature, 14 Aug. 2003, v. 424, pp. 824-830, the teachings of which are incorporated herein by reference in its entirety.

Bio-analytical system 500 has a flow cell 510 appropriately connected to a pump (not explicitly shown in FIG. 5). In one embodiment, flow cell 510 can be connected to the pump in a manner similar to that indicated in FIG. 1A for flow cell 110. One wall of flow cell 510 is formed by a side 512 of a prism 520. The surface of side 512 facing the flow channel of flow cell 510 has a target-receptor layer 562 that is similar to target-receptor layer 262 (FIG. 2). More specifically, target-receptor layer 562 comprises a plurality of target receptors 504 attached to a metal film 502. Target receptors 504 are designed to bind a target substance 514 as indicated in FIG. 5.

Bio-analytical system 500 further has a light source 518 configured to illuminate the back surface of side 512 through the body of prism 520. The light that is reflected from side 512 is detected by a detector array 522 to determine an incidence angle at which SPs are generated most efficiently in target-receptor layer 562, hereafter termed the "critical SP angle." The critical SP angle manifests itself through the diminished intensity of the corresponding specularly reflected beam. When target-receptor layer 562 is exposed to an analyte that can bind to target receptors 504, the binding event can be observed as a change of the critical SP angle, e.g., from angle $\theta_1$ to angle $\theta_2$, as indicated in FIG. 5. This change is measured using detector array 522, and the measurement result is used to determine the amount of target substance 514 bound to target-receptor layer 562.

When the analyte contains one or more non-target substances that can bind to target receptors 504 of target-receptor layer 562, e.g., in a manner similar to that illustrated in FIG. 2A, the change of the critical SP angle might contain a false-positive component corresponding to a bound non-target substance. However, similar to bio-analytical system 100, bio-analytical system 500 exploits the difference between the binding strengths of target substance 514 and a non-target substance to enhance the specificity of detection for the target substance. More specifically, by appropriately selecting a volumetric flow rate through flow cell 510, bio-analytical system 500 dislodges at least some of the bound non-target substance from target-receptor layer 562, thereby reducing the corresponding false-positive component. Calibration procedures similar to those described above in reference to FIGS. 3A-B can be used to advantageously configure bio-analytical system 500 for optimal detection of various target substances.

Figure 6A:
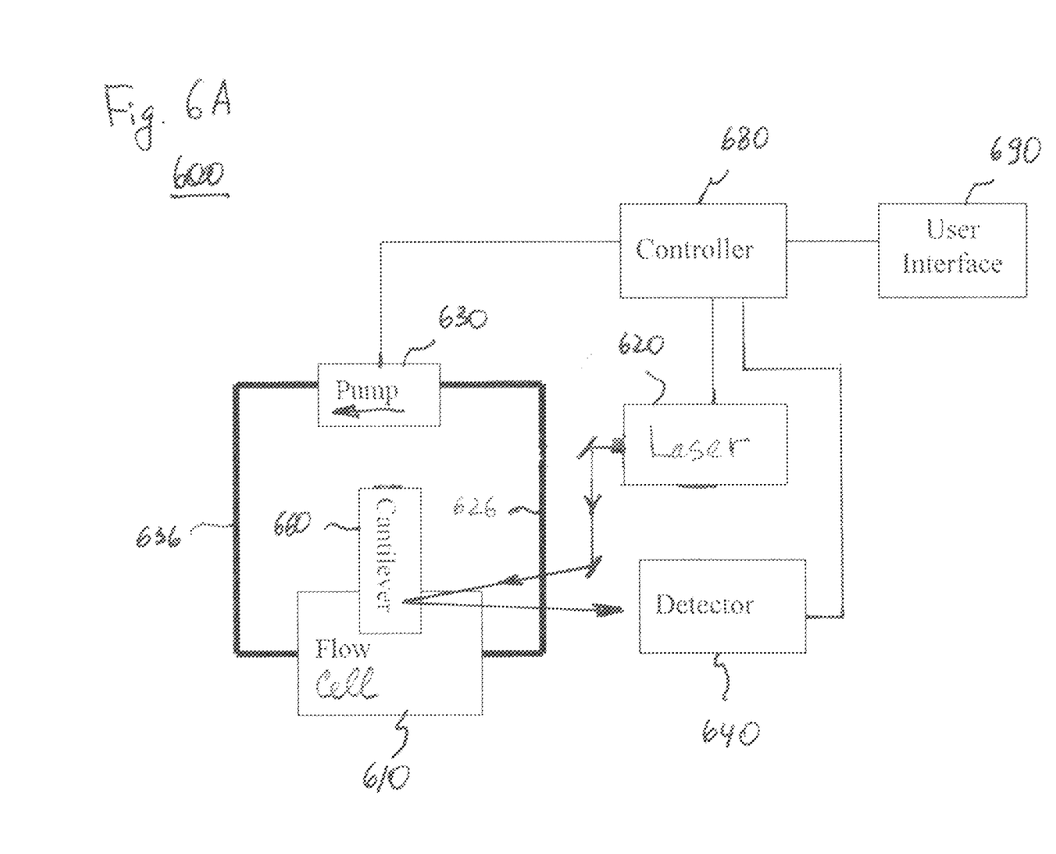
FIGS. 6A-C schematically show a bio-analytical system according to yet another embodiment of the invention.
Figure 6B:
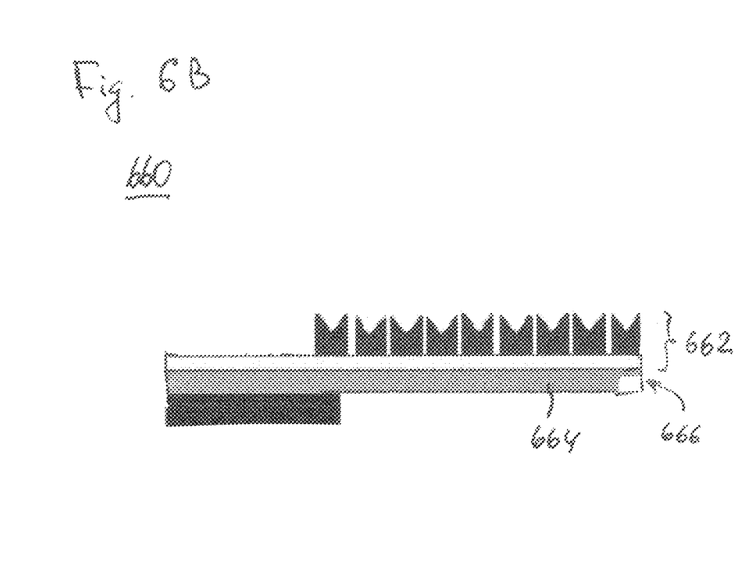
Figure 6C:
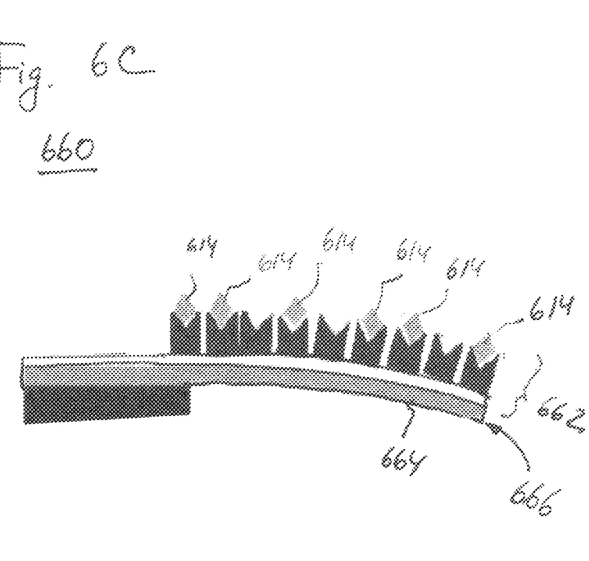

FIGS. 6A-C schematically show a bio-analytical system 600 according to yet another embodiment of the invention. More specifically, FIG. 6A shows a block diagram of bio-analytical system 600. FIGS. 6B-C show pictorial side views of a cantilever sensor 660 used in bio-analytical system 600. Bio-analytical system 600 has many components that are analogous to the corresponding components of bio-analytical system 100 (FIG. 1), with the analogous components of the two systems being designated with labels having the same last two digits. As such, for a general description of the components of bio-analytical system 600 that have analogues in bio-analytical system 100, the reader is referred to the description of FIGS. 1A-C above. Relevant differences between bio-analytical systems 100 and 600 are described in more detail below.

Referring to FIGS. 6A and 6B, cantilever sensor 660 differs in several aspects from cantilever sensor 150 (FIG. 1B). One aspect is that cantilever sensor 660 is designed to be interrogated optically and, as such, does not require electrical connections and does not have a piezoelectric transducer. A laser 620 and an optical detector (e.g., a charge-coupled device (CCD)) 640 are used in bio-analytical system 600 to optically interrogate cantilever sensor 660 as further described below. Another aspect is that a cantilever portion 664 of cantilever sensor 660 has a target-receptor layer 662 only on one side, as opposed of having it on at least two sides (for comparison, see target-receptor layer 162 shown in FIG. 1B).

Prior to being exposed to a target substance 614, cantilever portion 664 is substantially flat as indicated in FIG. 6B. However, when target substance 614 binds to target-receptor layer 662, it changes mechanical characteristics of the target-receptor layer. This change produces a stress gradient between target-receptor layer 662 and cantilever portion 664, which causes the target-receptor layer and the cantilever portion to deform as indicated in FIG. 6C. The extent of this deformation is measured optically, as known in the art, using laser 620 and optical detector 640. For example, the following characteristics of the deformed cantilever portion 664 can be used to quantify the deformation: (1) displacement of an edge 666 with respect to the edge's reference position shown in FIG. 6B; (2) deflection angle, e.g., measured near edge 666; and (3) the curvature profile along the longitudinal direction (which is orthogonal to edge 666). In effect, the flat configuration of cantilever portion 664 shown in FIG. 6B serves as a reference state with respect to which the deformation is measured. The measurement results are then used to determine the amount of target substance 614 bound to target-receptor layer 662.

When the analyte, to which cantilever sensor 660 is exposed, contains one or more non-target substances that can bind to target-receptor layer 662, e.g., in a manner similar to that illustrated in FIG. 2A, the deformation of cantilever portion 664 might contain a false-positive component corresponding to a bound non-target substance. However, by appropriately selecting a volumetric flow rate through flow cell 610, bio-analytical system 600 dislodges at least some of the bound non-target substance from target-receptor layer 662, thereby reducing the corresponding false-positive component. Calibration procedures similar to those described above in reference to FIGS. 3A-B can be used to advantageously configure bio-analytical system 600 for optimal detection of various target substances.

Additional label-free biochemical assays that could benefit from various embodiments of the present invention might be based on quartz-crystal-microbalance (QCM) and fiber-optic-biosensing (FOBS) technologies. The QCM technology has certain similarities with the above-described cantilever technology. The FOBS technology has some similarities with the above-described SPR technology. In particular, the FOBS technology relies on the evanescent field, which is present outside of the fiber core, to sense changes in the refractive index at the functionalized external surface of the fiber.

While this invention has been described with reference to illustrative embodiments, this description is not intended to be construed in a limiting sense. For example, while bio-analytical system 100 has been described above as having a single cantilever sensor 150, the system can be modified to have two or more arrayed cantilever sensors, with at least some of the sensors being functionalized for different target substances and/or reference measurements. Various modifications of the described embodiments, as well as other embodiments of the invention, which are apparent to persons skilled in the art to which the invention pertains are deemed to lie within the principle and scope of the invention as expressed in the following claims. In particular, the scope of the invention is indicated by the appended claims rather than by the description and figures herein. All changes that come within the meaning and range of equivalency of the claims are to be embraced within their scope.

Unless explicitly stated otherwise, each numerical value and range should be interpreted as being approximate as if the word "about" or "approximately" preceded the value of the value or range.

It will be further understood that various changes in the details, materials, and arrangements of the parts which have been described and illustrated in order to explain the nature of this invention may be made by those skilled in the art without departing from the scope of the invention as expressed in the following claims.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

Throughout the detailed description, the drawings, which are not to scale, are illustrative only and are used in order to explain, rather than limit the invention. The use of terms such as height, length, width, top, bottom, is strictly to facilitate the description of the invention and is not intended to limit the invention to a specific orientation. For example, height does not imply only a vertical rise limitation, but is used to identify one of the three dimensions of a three dimensional structure as shown in the figures. Such "height" would be vertical where the electrodes are horizontal but would be horizontal where the electrodes are vertical, and so on. Similarly, while all figures show the different layers as horizontal layers such orientation is for descriptive purpose only and not to be construed as a limitation.

Also for purposes of this description, the terms "couple," "coupling," "coupled," "connect," "connecting," or "connected" refer to any manner known in the art or later developed in which energy is allowed to be transferred between two or more elements, and the interposition of one or more additional elements is contemplated, although not required. Conversely, the terms "directly coupled," "directly connected," etc., imply the absence of such additional elements.

What is claimed is:

1. A method of analyzing an analyte, the method comprising:
    (A) exposing a target-receptor layer that comprises a plurality of target receptors adapted to bind a target substance selected from bacteria and spores in a fluid that comprises the analyte including the target substance; and
    (B) performing label-free interrogation of the target-receptor layer for a presence of the target substance bound thereto while subjecting the target-receptor layer to a laminar flow of the fluid flowing at a flow speed in a range of from 2.7 mm/s to 4.05 mm/s that is controlled based on calibration data for the selectivity of binding of the target substance relative to binding of at least one non-target substance that can interfere with detection of the target substance by binding to the target receptors thereby providing a higher specificity of detection of the target substance in the analyte compared to a corresponding specificity of detection with the fluid being stationary, and
    wherein the target substance is a spore of *Bacillus anthraces*.

2. The method of claim 1, wherein:
    the target-receptor layer is disposed on a surface of a planar structure; and
    step (B) comprises:
        placing the planar structure in a middle portion of a flow cell with the target-receptor layer being at least partially immersed in the fluid; and
        pumping the fluid through the flow cell to produce the laminar flow of the fluid near the surface.

3. The method of claim 2, wherein:
the planar structure comprises a first side and a second side opposite to the first side; and
each of the first and second sides has a respective portion of the target-receptor layer.

4. The method of claim 2, wherein step (B) further comprises:
inducing a mechanical oscillation of the planar structure using a piezoelectric transducer attached to the planar structure; and
determining a resonance frequency of the oscillation which is dependent on the presence of the target substance.

5. The method of claim 2, wherein:
the planar structure is a piezoelectric transducer; and
step (B) further comprises:
electrically inducing a mechanical oscillation of the piezoelectric transducer; and
determining a resonance frequency of the oscillation which is dependent on the presence of the target substance.

6. The method of claim 1, wherein a target receptor from the plurality comprises an antibody corresponding to the target substance.

7. The method of claim 1, wherein step (B) comprises selecting the flow speed for the flow based on calibration data corresponding to the target substance.

8. The method of claim 1, wherein:
the target-receptor layer is disposed on a surface of a planar structure and comprises an antibody corresponding to the target substance; and
step (B) comprises:
(B1) placing the planar structure in a middle portion of a flow cell with the target-receptor layer being at least partially immersed in the fluid;
(B2) selecting the flow speed;
(B3) pumping the fluid through the flow cell at the selected flow speed;
(B4) inducing a mechanical oscillation of the planar structure using a piezoelectric transducer attached to the planar structure;
(B5) determining a resonance frequency of the oscillation; and
(B6) processing data collected in step (B5) to determine whether the target substance is present in the target-receptor layer.

9. The method of claim 8, further comprising the step of:
(C) determining a range of flow speeds for use in step (B) using a calibration procedure.

10. The method of claim 9, wherein step (C) comprises:
(C1) exposing the target-receptor layer to a test fluid comprising a specific non-target substance;
(C2) performing label-free interrogation of the target-receptor layer for a false-positive signal corresponding to the specific target substance bound thereto while subjecting the target-receptor layer to a flow of the test fluid; and
(C3) repeating step (C2) for each flow speed selected from a predetermined plurality of flow speeds.

11. A bio-analytical system, comprising:
means for exposing a target-receptor layer that comprises a plurality of target receptors adapted to bind a target substance in a fluid that comprises the analyte including the target substance selected from bacteria and spores; and
means for performing label-free interrogation of the target-receptor layer for a presence of the target substance bound thereto while subjecting the target-receptor layer to a laminar flow of the analyte-containing fluid flowing at a flow speed in a range of from 2.7 mm/s to 4.05 mm/s that is controlled based on calibration data for selectivity of binding of the target substance relative to binding of at least one non-target substance that can interfere with detection of the target substance by binding to the target receptors thereby providing a higher specificity of detection of the target substance in the analyte compared to a corresponding specificity of detection with the fluid being stationary, and
wherein the target substance is a spore of *Bacillus anthraces*.

12. A method of analyzing an analyte, the method comprising:
(A) exposing a target-receptor layer that comprises a plurality of target receptors adapted to bind a target substance in a fluid that comprises the analyte including the target substance; and
(B) performing label-free interrogation of the target-receptor layer for a presence of the target substance bound thereto while subjecting the target-receptor layer to a laminar flow of the fluid flowing at a flow speed in a range of from 2.7 mm/s to 4.05 mm/s that is controlled based on calibration data for the selectivity of binding of the target substance relative to binding of at least one non-target substance that can interfere with detection of the target substance by binding to the target receptors thereby providing a higher specificity of detection of the target substance in the analyte compared to a corresponding specificity of detection with the fluid being stationary, and
wherein the target substance is a spore of *Bacillus anthraces* and the at least one non-target substance is selected from one or more of a spore of *B. thuringiensis*, a spore of *B. cereus*, and a spore of *B. subtilis*.

13. A bio-analytical system, comprising:
means for exposing a target-receptor layer that comprises a plurality of target receptors adapted to bind a target substance in a fluid that comprises the analyte including the target substance; and
means for performing label-free interrogation of the target-receptor layer for a presence of the target substance bound thereto while subjecting the target-receptor layer to a laminar flow of the analyte-containing fluid flowing at a flow speed in a range of from 2.7 mm/s to 4.05 mm/s that is controlled based on calibration data for selectivity of binding of the target substance relative to binding of at least one non-target substance that can interfere with detection of the target substance by binding to the target receptors thereby providing a higher specificity of detection of the target substance in the analyte compared to a corresponding specificity of detection with the fluid being stationary, and
wherein the target substance is a spore of *Bacillus anthraces* and the at least one non-target substance is selected from one or more of a spore of *B. thuringiensis*, a spore of *B. cereus*, and a spore of *B. subtilis*.

* * * * *